United States Patent [19]

Watanabe et al.

[11] Patent Number: 5,167,234

[45] Date of Patent: Dec. 1, 1992

[54] ULTRASONIC PROBE HAVING ROTARY REFRACTING MEMBER

[75] Inventors: Kazuhiro Watanabe, Tokyo; Kenichi Hayakawa, Kawasaki; Hiroshi Ishikawa, Yokohama; Yasushi Hara; Kiyoto Matsui, both of Kawasaki; Kenji Kawabe, Yokohama; Takaki Shimura, Machida, all of Japan

[73] Assignee: Fujitsu Limited, Kanagawa, Japan

[21] Appl. No.: 668,553

[22] Filed: Mar. 13, 1991

[30] Foreign Application Priority Data

Mar. 20, 1990 [JP] Japan .................................. 2-72393

[51] Int. Cl.⁵ .............................................. A61B 8/00
[52] U.S. Cl. ......................... 128/662.06; 128/662.03; 128/660.09; 128/660.10; 73/606
[58] Field of Search ...................... 128/660.09, 660.10, 128/662.02, 662.03, 662.06, 660.08, 660.07; 73/606, 633

[56] References Cited

U.S. PATENT DOCUMENTS

| | | | |
|---|---|---|---|
| 4,131,022 | 12/1978 | Mezrich | 128/660.07 |
| 4,174,634 | 11/1979 | Dory | 73/606 |
| 4,762,002 | 8/1988 | Adams | 128/660.08 |
| 4,858,613 | 8/1989 | Fry et al. | 128/662.06 |
| 4,961,176 | 10/1990 | Tanaka et al. | 128/660.09 |
| 4,993,416 | 2/1991 | Ophir | 128/660.09 |
| 5,014,711 | 5/1991 | Nagasaki | 128/660.07 |

*Primary Examiner*—William E. Kamm
*Assistant Examiner*—George Manuel
*Attorney, Agent, or Firm*—Nikaido, Marmelstein, Murray & Oram

[57] ABSTRACT

An ultrasonic probe includes a housing, a piezoelectric element provided in the housing, the piezoelectric element emitting an ultrasonic beam, and a refracting member rotatably provided in the housing. The refracting member has a first surface opposite to the piezoelectric element and a second surface at which the ultrasonic beam emitted from the piezoelectric element and passing through the first surface is deflected in a state where a deflection angle between an axis perpendicular to a surface of the piezoelectric element and a deflected ultrasonic beam changes as the refracting member rotates.

34 Claims, 16 Drawing Sheets

FIG.IC PRIOR ART
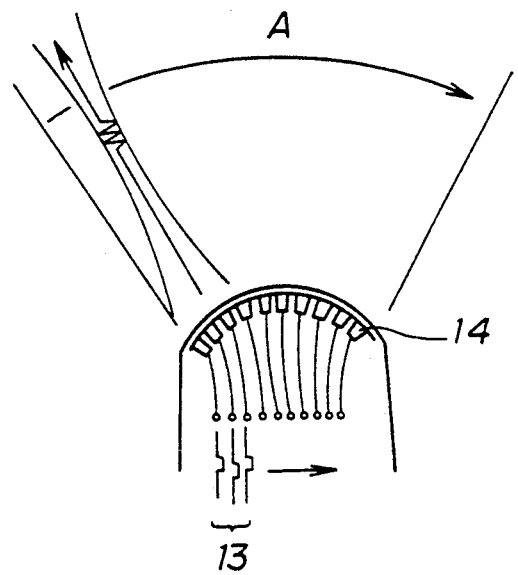
FIG.ID PRIOR ART  FIG.IE PRIOR ART
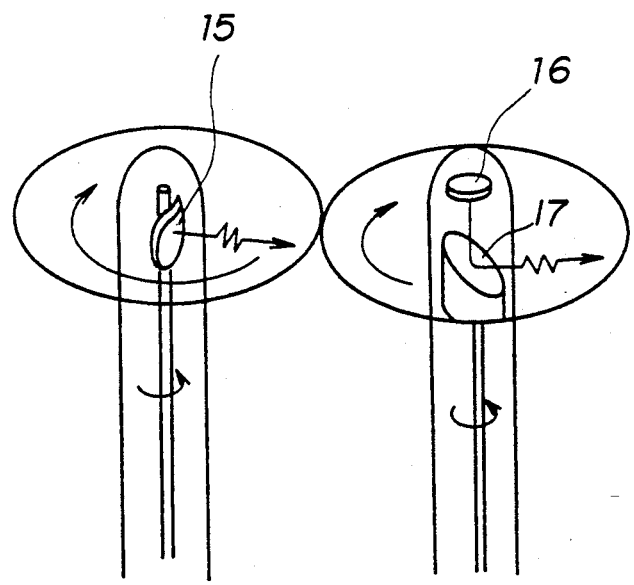

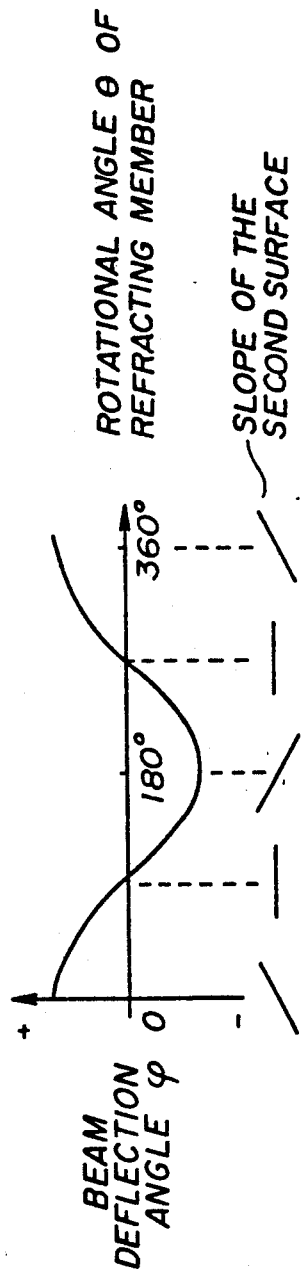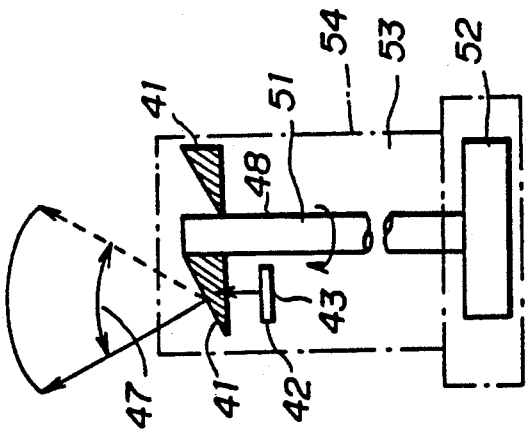
FIG.4B
FIG.4C

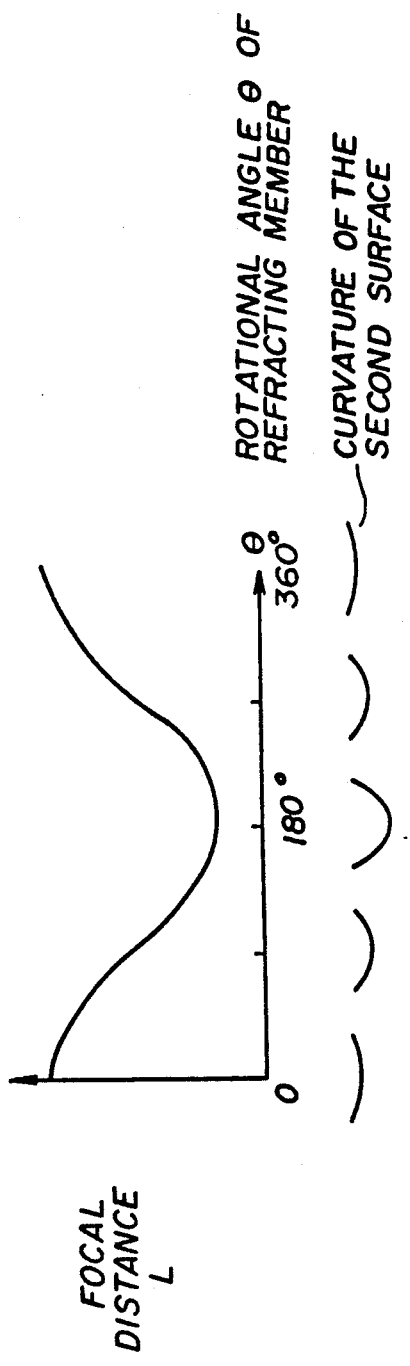
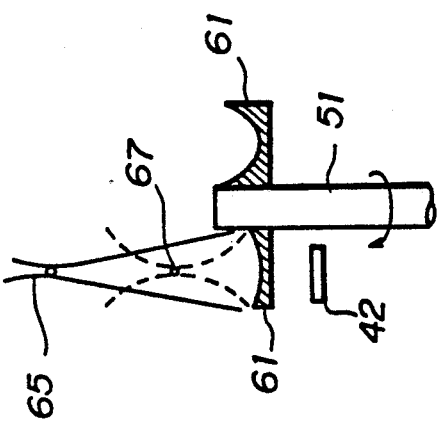
FIG.5B
FIG.5C

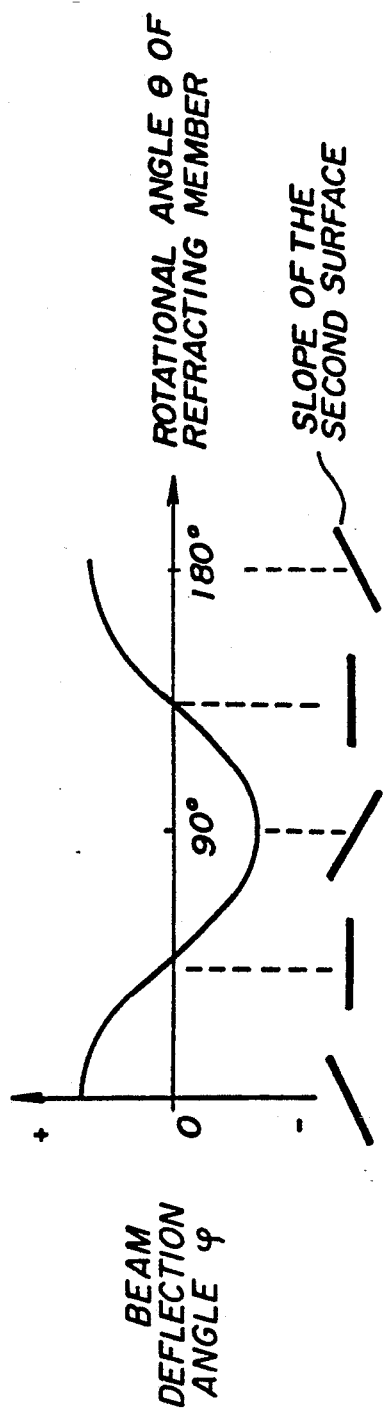

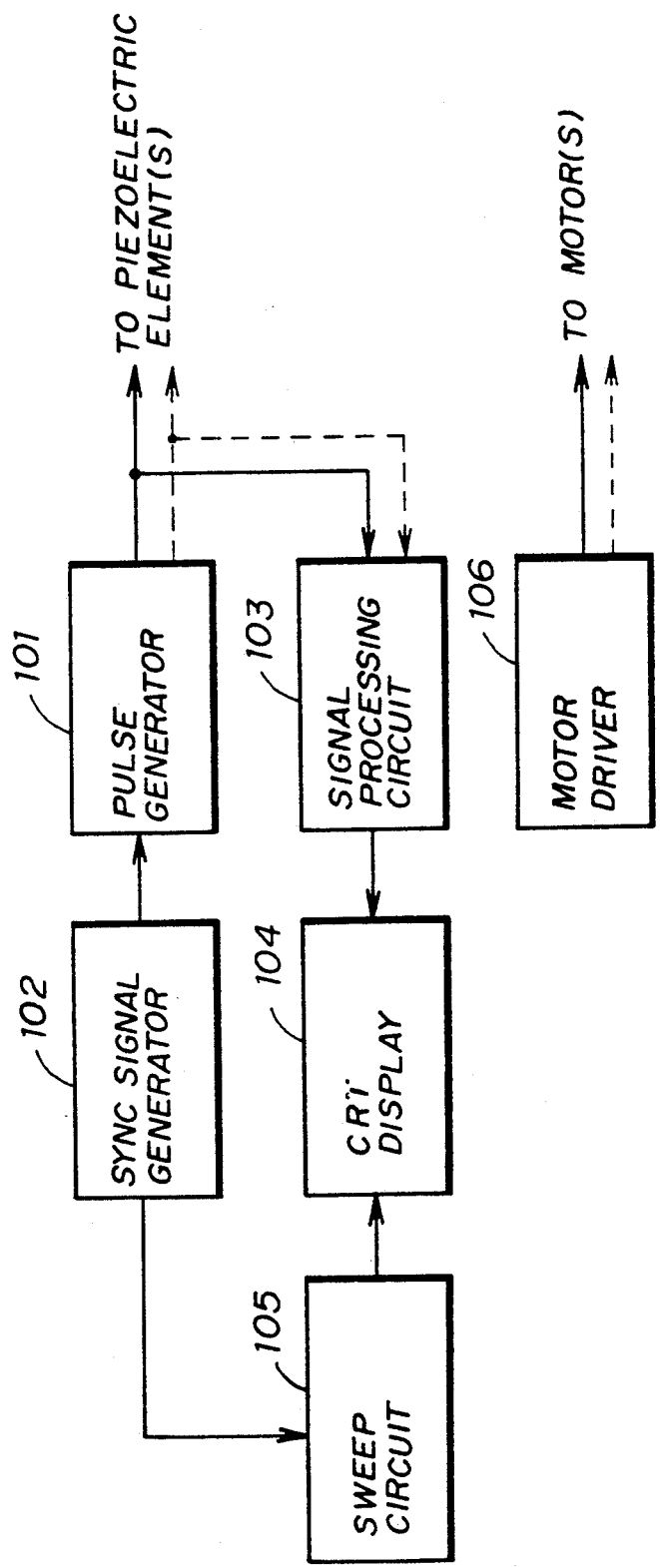

ULTRASONIC PROBE HAVING ROTARY REFRACTING MEMBER

BACKGROUND OF THE INVENTION

The present invention generally relates to an ultrasonic probe which projects an ultrasonic wave onto a living human body and receives a beam reflected from inside the body, so that information related to the body can be obtained from the reflected beam. More particularly, the present invention is concerned with an ultrasonic probe having a rotary refracting member.

Conventionally, a diagnostic method using an ultrasonic probe is used to obtain information inside of the living human body. An ultrasonic probe is inserted into a part of a living human body, for example, a blood vessel, and the inside thereof is scanned by an ultrasonic beam emitted from the ultrasonic probe.

FIG. 1A illustrates a first conventional ultrasonic probe, which has a plurality of piezoelectric elements 11 supported in a rotary disk. When the piezoelectric elements 11 are rotating, each of them emits an ultrasonic beam within a sectorial area A.

FIG. 1B illustrates a second conventional ultrasonic probe. A plurality of piezoelectric elements 12 are aligned and supplied with pulse signals 13 having mutually different element driving times, so that an ultrasonic beam is deflected in the sectorial area A.

FIG. 1C illustrates a third conventional ultrasonic probe. A plurality of piezoelectric elements 14 are arranged on a curved surface portion and are successively driven by the driving pulses, so that an ultrasonic wave, deflected in the sectorial area A, can be obtained.

FIG. 1D illustrates a fourth conventional ultrasonic probe. A piezoelectric element 15 emits an ultrasonic beam while it is being rotated, so that the ultrasonic beam is radially deflected.

FIG. 1E illustrates a fifth conventional ultrasonic probe. A piezoelectric element 16 emits a ultrasonic beam, which is reflected by a rotary reflector 17, so that the ultrasonic beam is radially deflected.

However, the above-mentioned first through fifth conventional ultrasonic probes have the following disadvantages. Since the piezoelectric elements are rotated, it is necessary to provide a magnetic coupling device which magnetically couples the piezoelectric elements with an external device. Thus, it is very difficult to produce a compact ultrasonic probe which is small enough to be inserted into a blood vessel having a diameter between approximately 3–10 mm.

It is also very difficult to produce a compact ultrasonic probe having the structure shown in FIG. 1B or FIG. 1C, because it is necessary to produce an array of small piezoelectric elements. In addition, it is very difficult to connect lead lines to the small piezoelectric elements.

It is possible to produce a compact ultrasonic probe having the structure shown in FIG. 1D or FIG. 1E. However, each of the ultrasonic probes shown in FIGS. 1D and 1E can only scan a plane substantially perpendicular to the rotating axis. Thus, it is impossible to obtain information related to an object located in front of the ultrasonic probe.

As shown in FIG. 2, a ultrasonic probe 22 used in the medical field is inserted into, for example, a blood vessel 21. In this state, it is required that an ultrasonic beam be forwardly emitted from the ultrasonic probe 22 in a sectorial area 23, so that two-dimensional or three-dimensional sectional images can be obtained.

On the other hand, as shown in FIG. 3, there is a need for an ultrasonic probe capable of focusing the ultrasonic beam at any point in a focus range 32 between focus points 33 and 34. Each of the structures shown in FIGS. 1B and 1C will meet such a need. However, as has been pointed out previously, it is very difficult to provide a compact ultrasonic probe.

SUMMARY OF THE INVENTION

It is an object of the present invention to provide a novel and useful ultrasonic probe in which the aforementioned disadvantages of the prior ultrasonic probes are eliminated.

This object of the present invention is achieved by an ultrasonic probe comprising: a housing; a piezoelectric element provided in the housing, the piezoelectric element emitting an ultrasonic beam; and a refracting member rotatably provided in the housing, the refracting member having a first surface opposite to the piezoelectric element and a second surface at which the ultrasonic beam emitted from the piezoelectric element and passing through the first surface is deflected in a state where a deflection angle between an axis perpendicular to a surface of the piezoelectric element and a deflected ultrasonic beam changes as the refracting member rotates.

The above-mentioned object of the present invention is also achieved by an ultrasonic probe comprising: a housing; a piezoelectric element provided in the housing, the piezoelectric element emitting an ultrasonic beam; a first refracting member rotatably provided in the housing, the first refracting member having a first surface opposite to the piezoelectric element and a second surface at which the ultrasonic beam emitted from the piezoelectric element and passing through the first surface is focused at different focal points during a time when one revolution of the refracting member is completed; and a second refracting member rotatably provided in the housing and opposite to the first refracting member so that the second refracting member has an axis identical to that of the first refracting member, the second refracting member having a third surface receiving the ultrasonic beam from the first refracting member, and a fourth surface at which the ultrasonic beam received by the third surface is deflected in a state where a deflection angle between an axis perpendicular to a surface of the piezoelectric element and a deflected ultrasonic beam emitted from the fourth surface changes as the second refracting member rotates.

BRIEF DESCRIPTION OF THE DRAWINGS

Other objects, features and advantages of the present invention will become more apparent from the following detailed description when read in conjunction with the accompanying drawings, in which:

FIGS. 1A, 1B, 1C, 1D and 1E are respectively diagrams of conventional ultrasonic probes;

FIGS. 4A, 4B, 4C and 4D are diagrams illustrating a first preferred embodiment of the present invention;

FIGS. 5A, 5B and 5C are diagrams illustrating a second preferred embodiment of the present invention;

FIGS. 9A, 9B, 9C and 9D are diagrams illustrating a sixth preferred embodiment of the present invention;

FIG. 10 is a block diagram of a control device for controlling the ultrasonic probe according to the present invention.

DESCRIPTION OF THE PREFERRED EMBODIMENTS

Figure 1A:
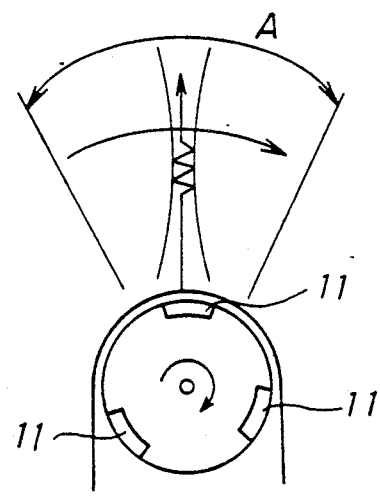
Figure 1B:
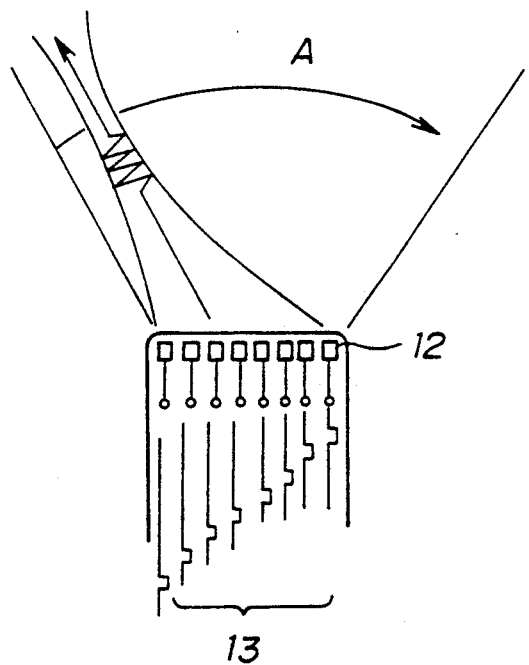
Figure 2:
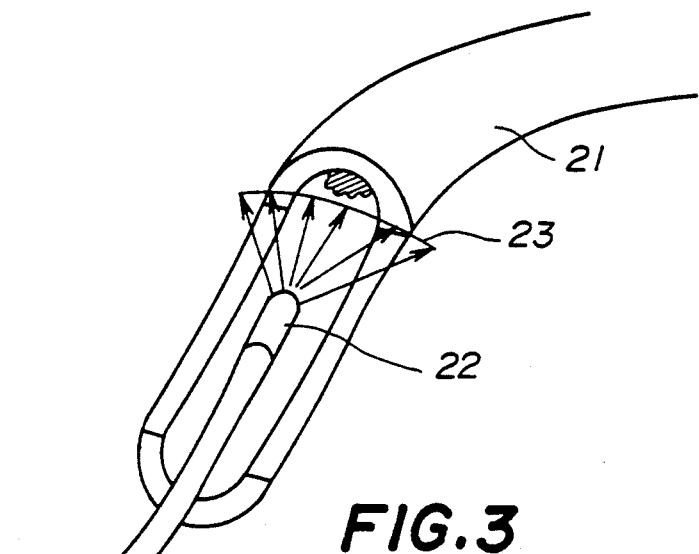
FIG. 2 is a perspective view of a medical application of the ultrasonic probe.
Figure 3:
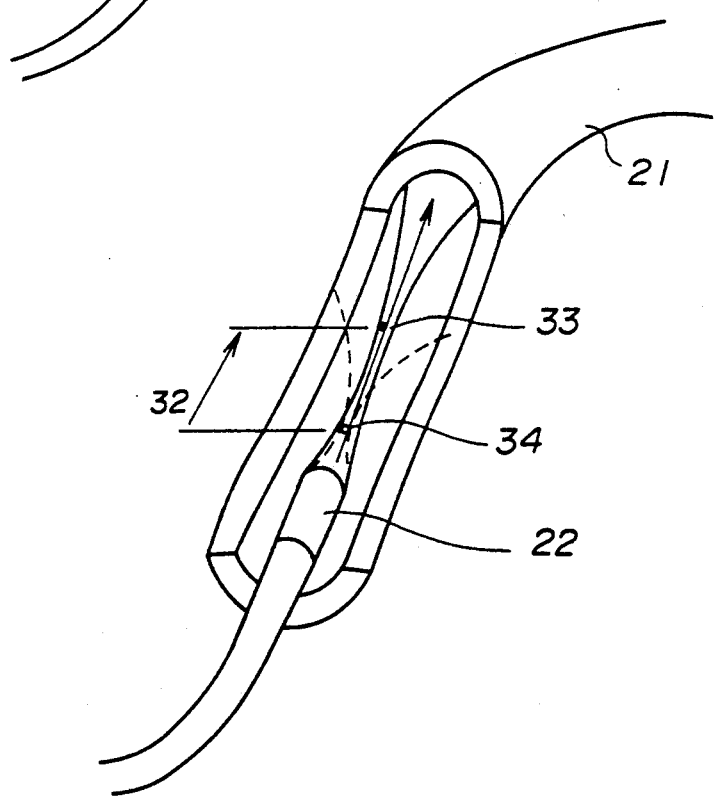
FIG. 3 is a perspective view showing a desired function of the ultrasonic probe.

A description will now be given of an ultrasonic probe according to a first preferred embodiment of the present invention with reference to FIGS. 4A, 4B, 4C and 4D.

Referring to these figures, the ultrasonic probe according to the first preferred embodiment of the present invention has a refracting member 41 and a piezoelectric element 42. The refracting member 41 has a central through hole with which a shaft 51 rotated by a motor 52 engages. The refracting member 41 is rotated around an axis a-a' of the shaft 51. The refracting member 41 has a first flat surface opposite to the piezoelectric element 42, and a second indulating or wavy surface opposite to the first flat surface. The plan view of the refracting member 41 has a substantially ring shape. The piezoeleotric element 42 has a disk shape. The first flat surface of the refracting member 41 has a size (length between an outer end and an inner end) sufficient to receive an ultrasonic beam emitted from the entire surface of the piezoelectric element 42. Two electrodes are formed on two opposite surfaces of the piezoelectric element 42. Two leads 43 are connected to the two electrodes. When a driving signal generated by an external device (not shown for the sake of simplicity) is applied to the piezoelectric element 42 via the leads 43 and the electrodes, the piezoelectric element 42 emits the ultrasonic beam along an axis 44 substantially perpendicular to the surfaces of the piezoelectric element 42.

The refracting member 41 is formed of a material having an acoustic impedance substantially identical of that of a living object. For example, when the ultrasonic probe is used for diagnosing the human body, it is preferable that the refracting member 41 be formed of a material having an acoustic impedance between $1 \times 10^6$ kg/m²s and $4 \times 10^6$ kg/m²s. With the above in mind, the refracting member 41 is formed of a material having, as a main component, silicon, epoxy, urethane, or polystyrene resin. The refracting member 41 is molded out of such a material, so that it is integrally formed. The diameter of the refracting member 41 is approximately 1.5 mm, for example, when it is designed to be inserted into a human blood vessel.

As shown in FIG. 4C, the refracting member 41 fixed to the shaft 51 is placed in a housing together with the piezoelectric element 42. The piezoelectric element 42 and the motor 52 are supported in the housing 54 by means of any suitable mechanism. A room of the housing 54 in which the motor 52 is provided is sealed from a room in which the refracting member 41 and the piezoelectric element 42 are provided. The latter rpom of the housing 54 is filled with an acoustic medium 53, such as a physiological salt solution. The refractive index of the refracting member 41 is different from that of the acoustic medium. The refracting member 41 is formed of, for example, PZT.

The second surface of the refracting member 41 is inclined with respect to the axis 48 of the ultrasonic beam so that the slope of the second surface connecting inner and outer ends of the refracting member 41 continuously changes or undulates as a rotational angle $\theta$ changes. In other words, an angle of the slope of the second surface with respect to the surface of the piezoelectric element 42 successively changes as the rotational angle $\theta$ changes. It should be noted that lines 46 depicted on the second surface of the refracting member 41 are imaginary lines for indicating the slope, that is, for showing how the second surface is inclined or undulates. It should also be noted that the refractory member 41 is integrally formed and is not physically segmented into parts along the lines 46.

Figure 4A:
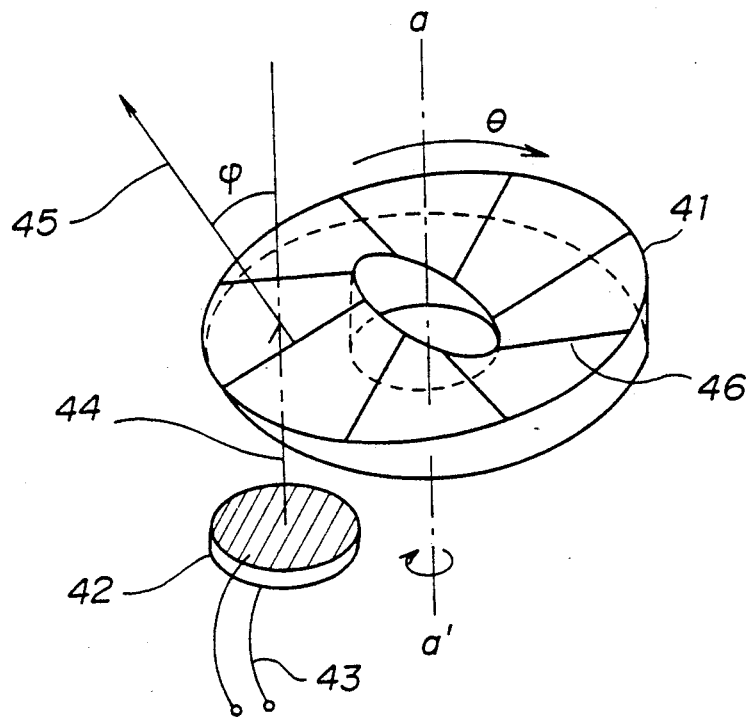

The slope of the second surface of the refracting member 41 will be described more specifically below. The ultrasonic beam emitted from the piezoelectric element 42 enters the refracting member 41 via its first surface and passes into the refracting member 41. The ultrasonic beam is then refracted at the second surface of the refracting member 41 by a deflection angle $\phi$. The deflection angle $\phi$ is defined between the ultrasonic beam axis 44 and the direction in which the refracted ultrasonic beam goes. In FIG. 4A, the ultrasonic beam is outward deflected.

FIG. 4B is a graph illustrating the relationship between the deflection angle $\phi$ and the rotational angle $\theta$ of the refracting member 41. FIG. 4B also shows a change in the slope of the second surface of the refracting member 41 as a function of the rotational angle $\theta$. When the ultrasonic beam is outward deflected with respect to the ultrasonic beam axis 44, the rotational angle $\theta$ has a positive value. On the other hand, the rotational angle $\theta$ has a negative value when the ultrasonic beam is inward deflected with respect to the ultrasonic beam. The rotational angle $\theta$ is zero when the refracting member 41 is located at a position shown in FIG. 4A.

When the rotational angle $\theta$ is 90°, the second surface of the refracting member 41 which receives the ultrasonic beam is horizontal (parallel to the surface of the piezoelectric element 42), so that the deflection angle $\phi$ is zero. When the rotational angle $\theta$ is 180°, the second surface of the refracting member 41 is inclined as shown in FIG. 4B, so that the ultrasonic beam is inward deflected. When the rotational angle $\theta$ is 270°, the second surface is horizontal (parallel to the surface of the piezoelectric element 42), so that the deflection angle $\phi$ is zero. It can be seen from the above that the ultrasonic beam is successively deflected as the rotational angle $\theta$ of the refracting member 41 changes so that a curve indicating a change in the deflection angle $\phi$ as a function of the rotational angle $\theta$ is like a sine curve. As a result, it is possible to deflect the ultrasonic beam within a sectorial area 47 in front of the leading end of the ultrasonic probe.

The refracting member 41 is rotated at a revolution speed sufficient to display an image generated from the received ultrasonic beam. For example, when the image is displayed on the CRT display, the refracting member 41 is rotated at, for example, 1800 rpm. It will be noted that such a revolution speed is greatly smaller than the propagation speed of the ultrasonic beam.

The driving signal is intermittently applied to the piezoelectric element 42 during a predetermined period. The ultrasonic beam from the refracting member 41 is reflected by an object and then received at almost the same position on the second surface of the refracting member. Then, the reflected ultrasonic beam is projected onto the piezoelectric element 42, so that a corresponding voltage is generated. This voltage is transferred to an external device via the lead lines 43. The external device forms, in a conventional way, a sectional image from data successively received from the piezoelectric element 43.

Figure 4D:
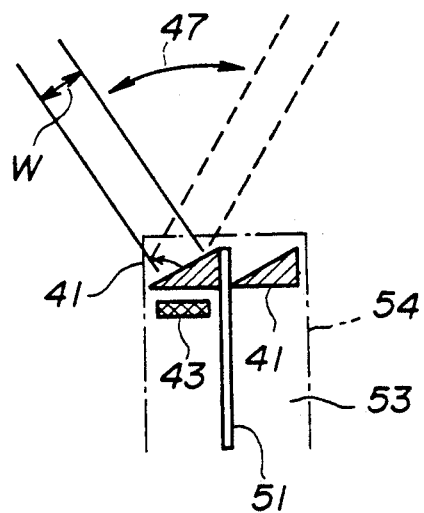

As shown in FIG. 4D, the deflected ultrasonic beam has a width W since the ultrasonic beam is emitted from the entire surface of the piezoelectric element 42.

A description will now be given of an ultrasonic probe according to a second preferred embodiment of the present invention with reference to FIGS. 5A, 5B and 5C, in which those parts which are the same as those shown in FIGS. 4A through 4E are given the same reference numerals. The housing 54 and the motor 52 are omitted from FIG. 5C for the sake of simplicity.

The ultrasonic probe according to the second preferred embodiment includes a refracting member 61 having a first flat surface opposite to the piezoelectric element 42 and a second curved surface. The imaginary lines 46 are depicted in order to show how the second curved surface is curved. The curvature of the second curved surface of the refracting member 61 successively changes as the rotational angle $\theta$ of the refracting member 61 changes. The ultrasonic beam emitted from the entire surface of the piezoelectric element 42 is deflected at the second curved surface of the refracting member 41 so that the degree of deflection is based on the curvature of the second surface which receives the ultrasonic beam. More specifically, as shown in FIG. 5A, the ultrasonic beam entering an outer portion of the second surface of the refracting member 61 is inwardly deflected, and the ultrasonic beam entering an inner portion thereof is outwardly deflected. The ultrasonic beam entering a central portion of the second surface of the refracting member 61 is not reflected because such a central portion is considered to be parallel to the surface of the piezoelectric element 42. It should be noted that the cross section of the refracting member 61 is symmetrical with respect to a line which passes through the central portion parallel to the ultrasonic beam axis 44.

Figure 5A:
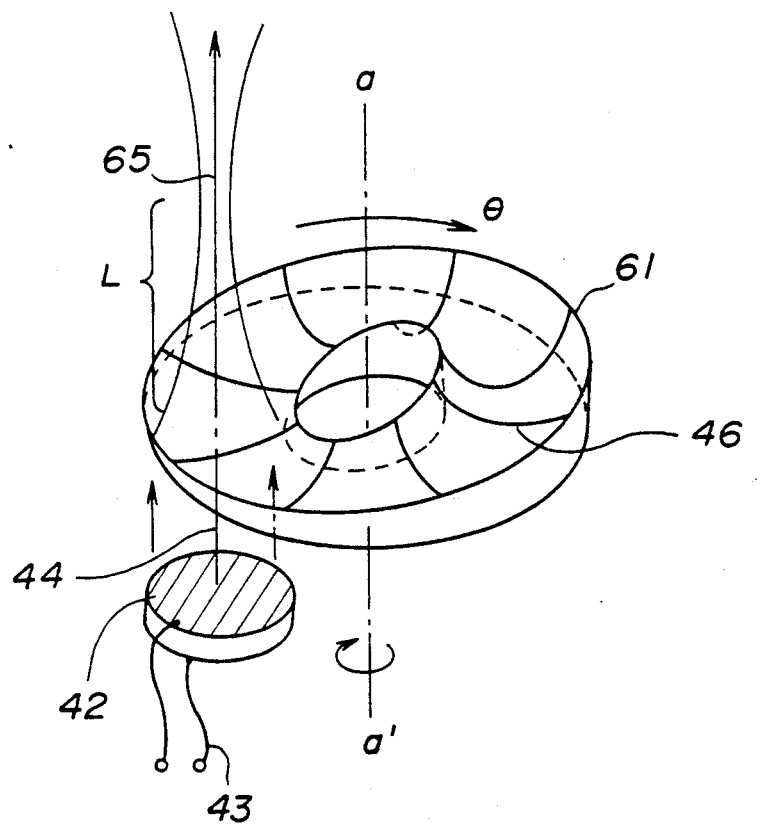

As shown in FIG. 5A, the ultrasonic beam is focused at a focal point 65 when the refracting member 61 is located at the position shown in FIG. 5A. A capital letter L shown in FIG. 5A denotes the focal distance obtained at this time. The curvature of the second surface of the refracting member 61 changes successively in accordance with a change in the rotational angle $\theta$ of the refracting member 61. Thus, as shown in FIG. 5B, the focal distance L also changes successively as the rotational angle $\theta$ changes. FIG. 5B also shows the curvature of the second surface of the refracting member 61 obtained at predetermined rotational angles. When the refracting member 61 is located at the position shown in FIG. 5A, the longest focal distance L is obtained with the rotational angle $\theta$ equal to zero. The focal distance L gradually decreases as the rotational angle $\theta$ increases. When the rotational angle $\theta$ is 180°, the shortest focal distance L is obtained. At this time, the ultrasonic beam is focused at a focal point 67, as shown in FIG. 5C. The broken lines shown in FIG. 5C show the deflected ultrasonic beam focused at the focal point 67. As the rotational angle $\theta$ further increases, the focal distance L increases. It can be seen from the above that the focal distance L changes within a range between the focal points 65 and 67, so that the curve showing the focal distance L as a function of the rotational angle $\theta$ is like a sine curve.

It should be noted that the refracting member 61 can be made stationary at a rotating angle which provides a desired focal length.

Figure 6A:
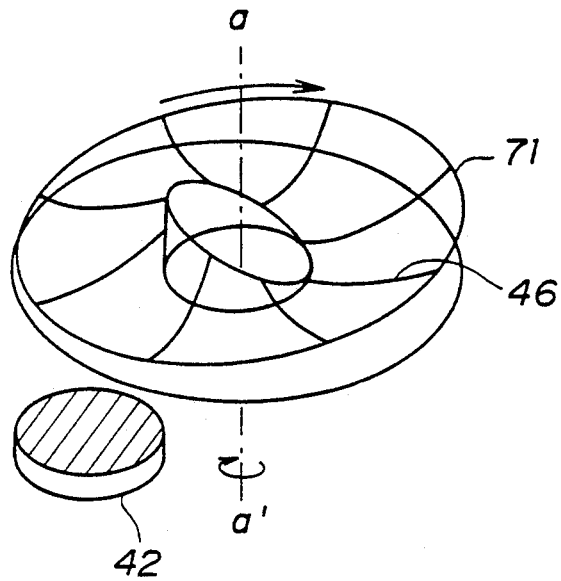
FIGS. 6A and 6B are diagrams illustrating a third preferred embodiment of the present invention.
Figure 6B:
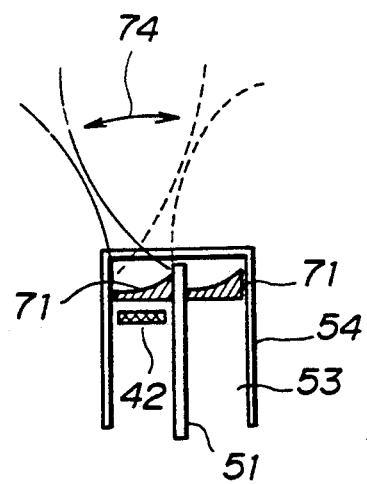

A description will now be given of an ultrasonic probe according to a third preferred embodiment of the present invention with reference to FIGS. 6A and 6B, in which those parts which are the same as those shown in the previous figures are given the same reference numerals. The motor 52 shown in FIG. 4C is omitted from FIG. 6B for the sake of simplicity. The ultrasonic probe according to the third preferred embodiment includes a refracting member 71, which has a first flat surface opposite to the piezoelectric element 42, and a second curved surface opposite to the first flat surface. The second curved surface of the refracting member 71 is obtained by providing the slope of the second surface of the refracting member 41 with a constant curvature. Thus, the cross sectional portion of the refracting member 71 on the left side of the shift 51 shown in FIG. 6B is the same as that on the right side thereof.

The curvature of the second surface of the refracting member 71 functions to focus the ultrasonic beam leaving the refracting member 71 at a fixed focal point. Further, the curved slope of the second surface of the refracting member 71 successively changes as the rotational angle $\theta$ changes, as shown in FIG. 4B. Thus, the focused ultrasonic beam is deflected within a sectorial area 74, as shown in FIG. 6B. The difference between the first and third embodiments of the present invention can be seen from FIGS. 4D and 6B.

Figure 7A:
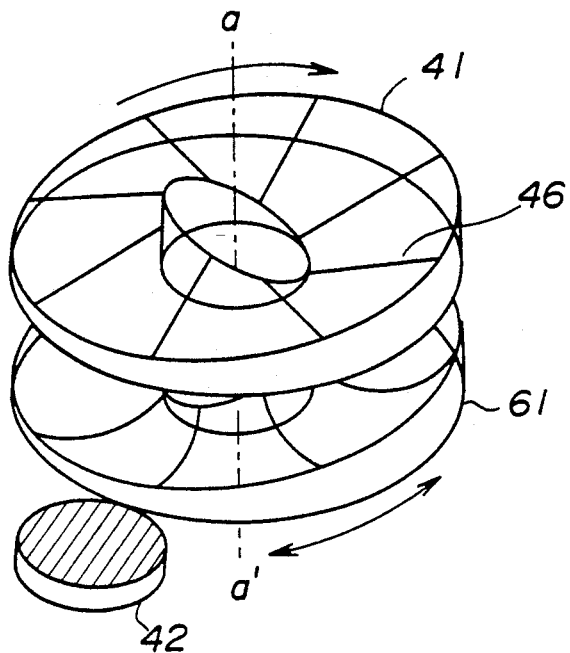
FIGS. 7A, 7B and 7C are diagrams illustrating a fourth preferred embodiment of the present invention.
Figure 7B:
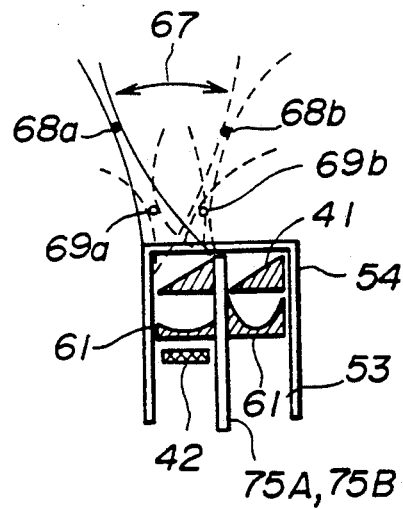
Figure 7C:
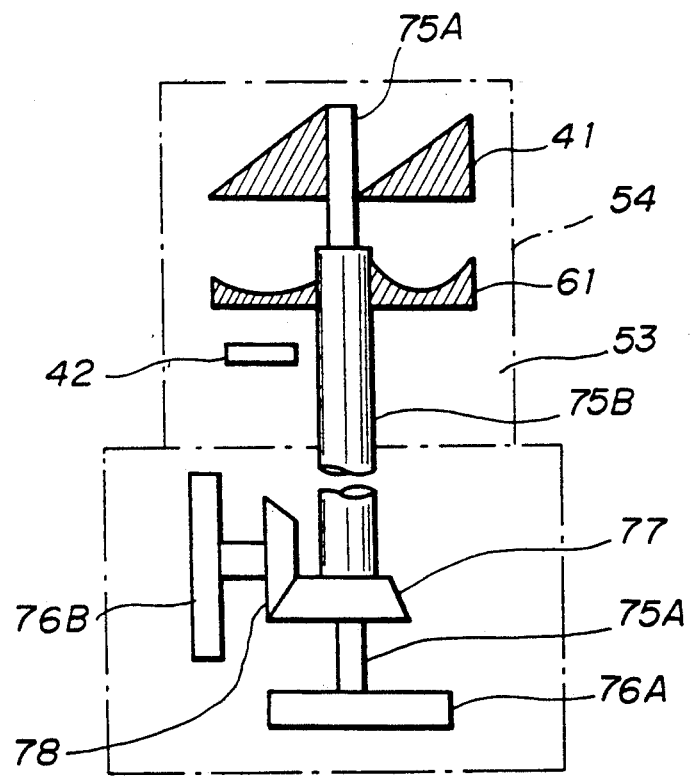

A description will now be given of a ultrasonic probe according to a fourth preferred embodiment of the present invention with reference to FIGS. 7A, 7B and 7C, in which those parts which are the same as those shown in the previous figures are given the same reference numerals. The fourth embodiment of the present invention corresponds to a combination of the aforementioned first and second embodiments of the present invention.

The ultrasonic probe according to the third preferred embodiment includes the two aforementioned refracting members 41 and 61. As shown in FIG. 7C, the refracting member 41 is fixed to a shaft 75A, and the refracting member 61 is fixed to a hollow shaft 75B. The shaft 75A penetrates the inside of the hollow shaft 75B. The shaft 75A is rotated by a motor 76A, and the hollow short 75B is rotated by a motor 76B via gears 77 and 78. The gear 77 is fixed to the hollow shaft 75B and the gear 78 is fixed to a shaft of the motor 76B. The refracting member 61 faces the piezoelectric element 42. Thus, the ultrasonic beam emitted from the piezoelectric element 42 passes through the refracting member 61 first and the refracting member 41 second. It may be possible to employ an alternative arrangement in which the positions of the refracting members 41 and 61 are interchanged with each other. However, it is preferable to use the arrangement of the refracting members 41 and 61 shown in FIG. 7C because the ultrasonic beam emitted from the piezoelectric element 42 passes through the refracting member 61 first, and thus the converged ultrasonic beam is efficiently input to the refracting member 41.

The refracting member 61 has the function of providing the variable local length as shown in FIG. 5C, and the refracting member 41 has the function of deflecting the ultrasonic beam in a sectorial area 67. The refracting members 61 and 41, which can be formed of an identical material, are rotated at an identical revolution in an identical direction, for example. The relative position of the refracting members 41 and 61 can be adjusted. The ultrasonic probe thus formed emits the focused ultrasonic beam within the sectorial area 67. A reference 68a indicates a focal point having the longest focal distance in the state where the deflection angle has the positive greatest value. A reference 69a indicates a focal point having the shortest focal distance in the same state. A reference 68b indicates a focal point having the longest focal distance in the state where the deflection angle is the negative greatest value. A reference 68b indicates a focal point having the shortest focal distance in the same state.

Figure 8A:
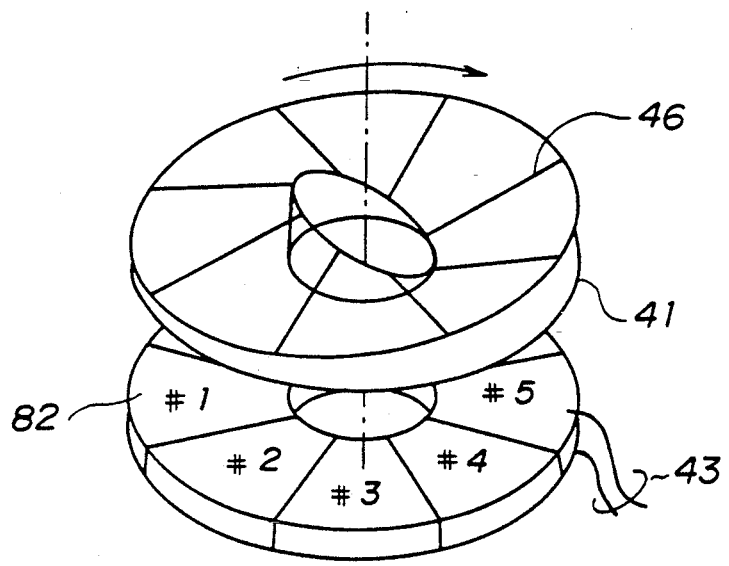
FIGS. 8A, 8B and 8C are diagrams illustrating a fifth preferred embodiment of the present invention.
Figure 8B:
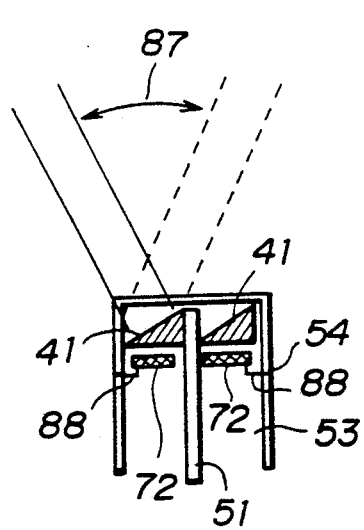

A description will now be given of an ultrasonic probe according to a fifth preferred embodiment of the present invention with reference to FIGS. 8A, 8B and 8C, in which those parts which are the same as those shown in the previous figures are given the same reference numerals. The ultrasonic probe according to the fifth preferred embodiment includes the aforementioned refracting member 41 and a ring-shaped piezoelectric element 82.

The ring-shaped piezoelectric element 82 has a plurality of divided piezoelectric element sections (some of which are labeled #1, #2, ..., #5). Two electrodes are respectively formed on opposite surfaces of each of the divided sections, and a pair of lead lines 43 is connected to the two respective electrodes. For the sake of simplicity, only one pair of the lead lines 43 is illustrated in FIG. 8A. With the above-mentioned arrangement, it is possible to separately drive the divided sections. The ring-shaped piezoelectric element 82 is fixed to an inner wall of the housing 53 by means of a suitable member 88. Various mechanisms for supporting piezoelectric elements have been known.

Figure 8C:
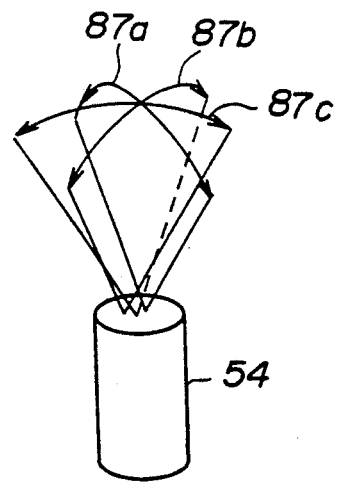

When one of the divided sections of the ring-shaped piezoelectric element 82 is driven in the state that the ring-shaped piezoelectric element 41 is rotating, the ultrasonic beam emitted therefrom is deflected in a corresponding two-dimensional sectorial area, for example, indicated by a reference 87a shown in FIG. 8C. When a different one of the divided sections is driven, the ultrasonic beam is deflected in a corresponding two-dimensional sectorial area, for example, indicated by a reference 87b shown in FIG. 8C. When a further different one of the divided sections is driven, the ultrasonic beam is deflected in a corresponding two-dimensional sectorial area, for example, indicated by a reference 87c shown in FIG. 8C. It will be seen from the above that the ultrasonic probe shown in FIGS. 8A through 8C is capable of deflecting the ultrasonic beam in the three-dimensional area. It will be noted that only one of the divided sections can be driven at one time. For example, the divided sections are successively driven one by one in the clockwise or counterclockwise direction by applying pulse signals generated by an external device (not shown) to the divided sections at different times. It is also possible to successively drive the divided sections one by one in a jumping drive procedure in which they are driven in the order of, for example, #1, #3, #5, ..., #2, #4, ...).

A description will now be given of an ultrasonic probe according to a sixth preferred embodiment of the present invention with reference to FIGS. 9A, 9B, 9C and 9D in which those parts which are the same as or similar to those shown in the previous figures are given the same reference numerals. The sixth embodiment is a catheter which functions as the ultrasonic probe with an instrument which eliminates a foreign substance on, for example, a blood vessel wall.

The ultrasonic probe according to the sixth embodiment includes a refracting member 91 fixed to a catheter body 95 (FIG. 9B) and the aforementioned ring-shaped piezoelectric element 82 having a plurality of divided sections now labeled 821. The refracting member 91 has a first flat surface opposite to the ring-shaped piezoelectric element 82, and a second surface. The second surface is so shaped that the relationship between the deflection angle $\phi$ and the rotational angle $\theta$ shown in FIG. 9D can be obtained. That is, the refracting member 91 provides the same relationship as that shown in FIG. 4B when it rotates by the ½ revolution. For example, when the rotational angle $\theta$ is 45° or 135°, the second surface located at the position at which the ultrasonic beam is received, is substantially horizontal (parallel to the surface of the ring-shaped piezoelectric element 82). It will be noted that the change of the deflection angle $\phi$ is obtained twice each time one revolution is completed.

Figure 9A:
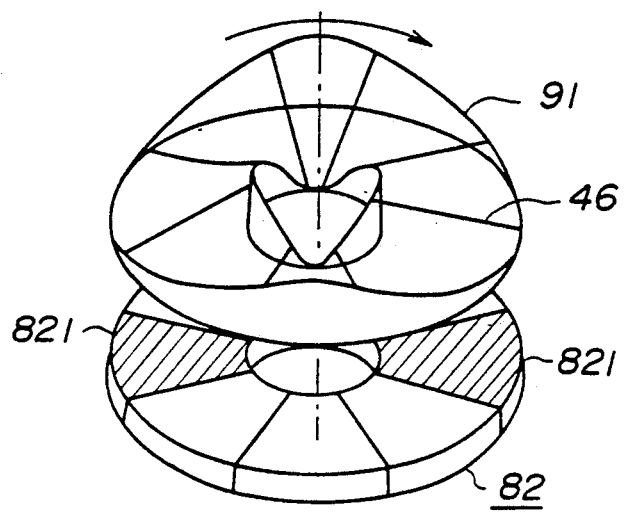
Figure 9B:
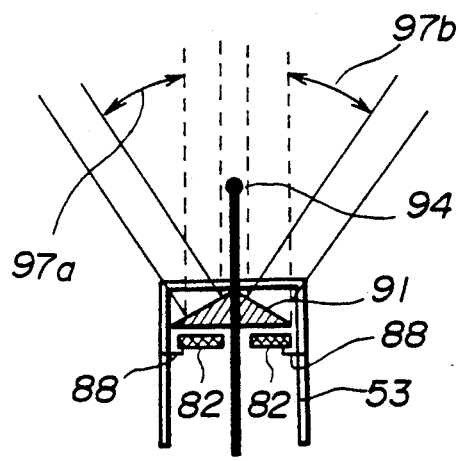
Figure 9C:
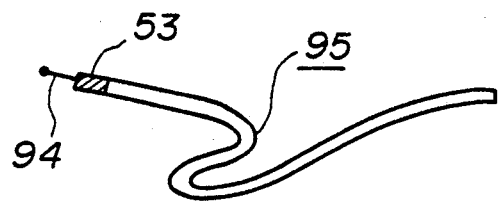

When the hatched divided section 821 of the ring-shaped piezoelectric element 82 on the left side of the drawing is driven during the time when the positive deflection angle $\phi$ at which the ultrasonic beam is outwardly deflected is obtained, as shown in FIG. 9B, the ultrasonic beam is deflected in an area 97a. On the other hand, when the hatched divided section 821 on the right side of the drawing is driven during the time when the positive deflection angle $\phi$ is obtained, the ultrasonic beam is deflected in an area 97b. It should be noted that the above deflection beams related to the two divided sections 821 are not projected onto the instrument 94. Thus, the scanning is not prevented due to the existence of the instrument 94 which projects from the front surface of the housing 53.

When two of the divided sections 821 are repeatedly driven, the two-dimensional sector scan having two scanning areas as shown in FIG. 9B can be obtained. On the other hand, by suitably selecting two of the divided sections 821 to be driven, it becomes possible to realize the three-dimensional scan. However, only one or two divided sections 821 can be used. In this case, only the two-dimensional sector scan can be obtained.

Figure 11:
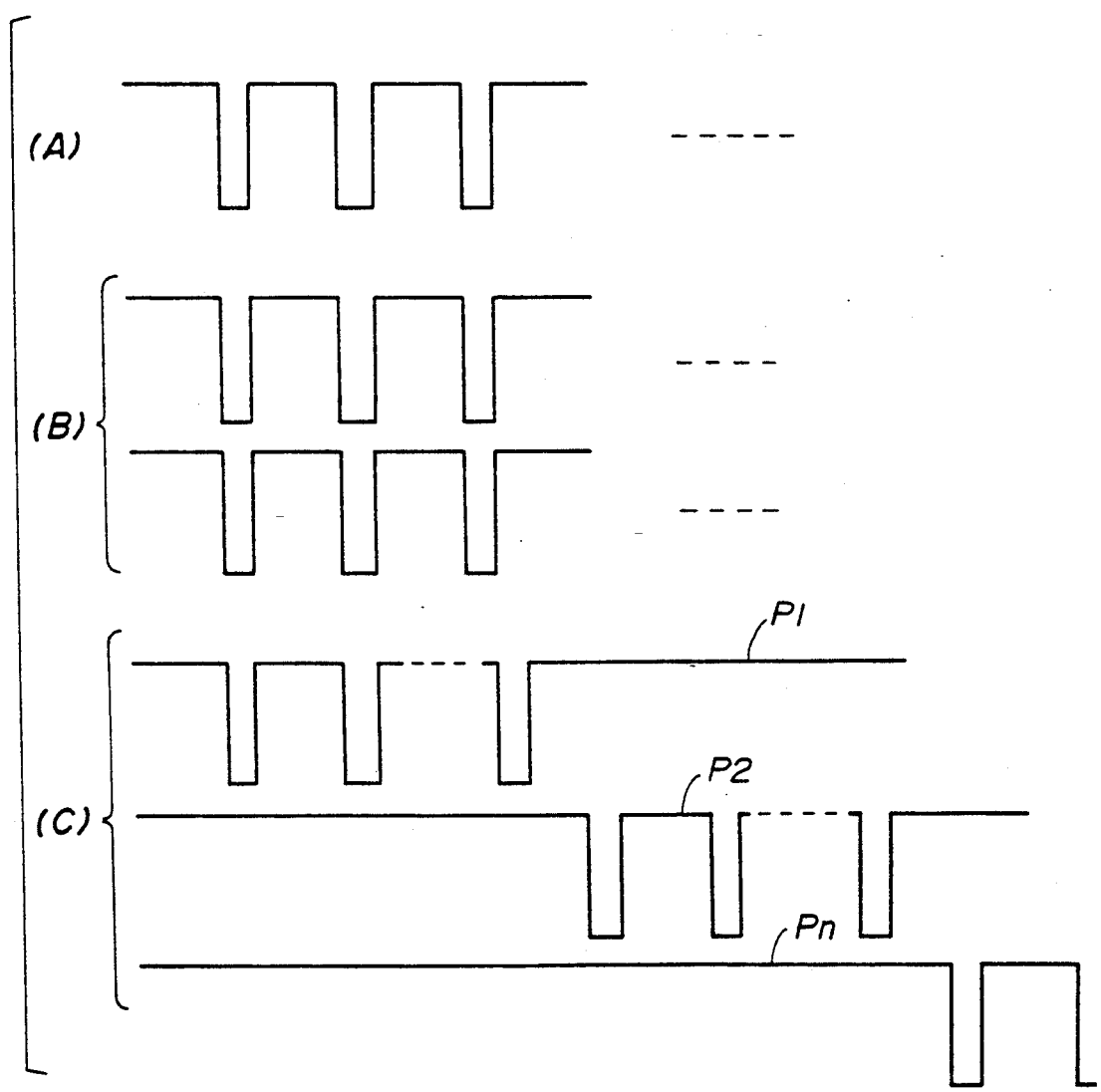
FIG. 11 is a waveform diagram illustrating pulses applied to piezoelectric elements used in the ultrasonic probes according to the embodiments of the present invention.

FIG. 10 illustrates a control device coupled to the ultrasonic probe according to the present invention. The control device shown in FIG. 10 is made up of a pulse generator, a synchronizing signal generator 102, a signal processing circuit 103, a CRT display device 10-4, a sweep circuit 105 and a motor driver 106. The synchronizing signal generator 102 generates a synchronizing signal and supplies it to the pulse generator 101 and the sweep circuit 105. The pulse generator 101 generates a pulse signal or pulse signals in response to the synchronizing signal 102. For example, the pulse generator 101 intermittently generates a series of pulses, as shown in FIG. 11(A). Each pulse has a voltage equal to, for example, 100 volts, and a pulse duration of time equal to, for example, 0.05 microseconds. The series of pulse signals shown in FIG. 11(A) is applied to the first, second, third and four preferred embodiments of the present invention. As shown in FIG. 11(B), the pulse generator 101 can also generate two series of pulses which are applied to the two hatched divided sections of the piezoelectric element 82 shown in FIG. 9A. As shown in FIG. 11(C), the pulse generator 101 can also generate a plurality of series of pulses P1, P2, . . . , Pn provided for the respective divided sections of the piezoelectric element 82 shown in FIG. 8A. For example, the series of pulses P1 is applied to one of the divided sections, and then the series of pulses P2 is applied to another one of the divided sections.

Turning now to FIG. 10, the signal processing circuit 103 receives the reflected ultrasonic beam and generates a video signal therefrom in a conventional manner. For example, the reflected ultrasonic beam is varying during a period between 1 and 2 microseconds. The sweep circuit 105 generates a sweep signal in response to the synchronizing signal from the synchronizing signal generator 102, and outputs the sweep signal to the CRT display device 104. The CRT display device shows an image generated by the video signal in accordance with the sweep signal. The motor driver 106 generates a driving signal or signals applied to the aforementioned motor 52 or motors 76A and 76B.

The present invention is not limited to the specifically disclosed embodiments, and variations and modifications may be made without departing from the scope of the present invention.

What is claimed is:
1. An ultrasonic probe comprising:
   a housing;
   a piezoelectric element provided in said housing, said piezoelectric element having an emitting surface adapted for emitting an ultrasonic beam;
   a refracting member rotatably provided in said housing, said refracting member having (a) a first flat surface opposed to said piezoelectric element emitting surface adapted so that said ultrasonic beam passes through said first flat surface and (b) a second undulating surface from which said ultrasonic beam is deflected wherein a deflection angle between (a) an axis perpendicular to said emitting surface of said piezoelectric element and (b) said deflected ultrasonic beam changes as said refracting member rotates; and
   driving means for rotating said refracting member.
2. An ultrasonic probe as claimed in claim 1, wherein said second undulating surface of said refracting member is formed to have a slope which causes said deflection angle to change to form a sine wave curve as a function of a rotational angle of said refracting member during a time when one revolution of said refracting member is completed.
3. An ultrasonic probe as claimed in claim 1, wherein one end of said second undulating surface, appearing in a cross section of said refracting member, has a substantially straight slop.
4. An ultrasonic probe as claimed in claim 1, wherein:
   said refracting member has a hole therein so that said refracting member has a donut shape in a plan view of said refracting member;
   a portion, between an outer periphery of said refracting member and an inner periphery thereof defining said hole, has a length sufficient to receive said ultrasonic beam emitted from said piezoelectric element.

5. An ultrasonic probe as claimed in claim 1, wherein as said refracting member rotates, said second undulating surface of said refracting member appears to have a curvature which changes.
6. An ultraonic probe as claimed in claim 1, wherein said second undulating surface of said refracting member has a curvature which deflects said ultrasonic beam so that said deflected ultrasonic beam is focused.
7. An ultraonic probe as claimed in claim 1, wherein said second undulating surface of said refracting member has a curvature which deflects said ultrasonic beam so that said deflected ultrasonic beam is focused at different focal points during revoluation of said refracting member.
8. An ultrasonid probe as claimed in claim 1, wherein sais second undulating surface of said refracting member has a curvature which deflects said ultrasonic beam so that said deflected ultrasonic beam is focused, and said second undulating surface has a focal point, which appears to change to form a sine curve as a function of a rotational angle of said refracting member during a time when one revolution of said refracting member is completed.
9. An ultrasonic probe as claimed in claim 1, wherein said second undulating surface of said refracting member is formed to have a slope which deflects said ultrasonic beam in a sectorial area during revolution of said refracting member.
10. An ultrasonic probe as claimed in claim 1, wherein said second undulating surface of said refracting member is formed to have a slope having a curvature which focuses said ultrasonic beam and which deflects said ultrasonic beam in a sectorial area during revolution of said refracting member.
11. An ultrasonic probe as claimed in claim 1, wherein said piezoelectric element has a disk shape, and said ultrasonic beam is emitted from all portions of said emitting surface of said piezoelectric element opposite said first flat surface of said refracting member.
12. An ultrasonic probe as claimed in claim 1, wherein:
   said piezoelectric element has a plurality of divided sections;
   each of said divided sections separately emits the ultrasonic beam.
13. An ultrasonic probe as claimed in claim 12, wherein said piezoelectric element has a size such that all surfaces of said divided sections of said piezoelectric element are opposite to the first flat surface of said refracting member.
14. An ultrasonic probe as claimed in claim 12, wherein two of said divided sections of said piezoelectric element emit said ultrasonic beam together.
15. An ultrasonic probe as claimed in claim 12, wherein each of said divided sections emits the ultrasonic beam one after another in a predetermined order.
16. An ultrasonic probe as claimed in claim 12, wherein said piezoelectric element has a ring shape.
17. An ultrasonic probe as claimed in claim 1, wherein said second undulating surface of said refracting member is formed to have a slope which deflects said ultrasonic beam in a sectorial area during revolution of said refracting member.
18. An ultrasonic probe as claimed in claim 17, whereins aid second surface of said refracting member is formed to ahve a slope which causes said deflection angle to appear to change to form a sine curve as a function of a rotational angle of said refracting member when one-half revolution of said refracting member is completed.

19. An ultrasonic probe as claimed in claim 17, wherein:
said piezoelectric element has a first portion and a second portion;
said first and second portions emit first and second ultrasonic beams at an identical time in a state where said first and second ultrasonic beams pass through said first flat surface of said refracting member and are deflected at different portions on said second undulating surface of said refracting member, so that two substantially sectorial areas which have no overlapped portions are formed on said second undulating surface of said refracting member.

20. An ultrasonic probe as claimed in claim 19, further comprising ad evice which penetrates through a center portion of said refracting member and a center portion of said piezoelectric element and projects from a front surface of said housing, wherein said two substantially sectorial areas are located on both sides of said medical instrument.

21. An ultrasonic probe as claimed in claim 1, further comprising an acoustic medium provided in said housing so that said refract member and said piezoelectric element are surrounded by said acoustic medium.

22. An ultrasonic probe as claimed in claim 21, wherein said refracting member has a refractive index different from that of said acoustic medium.

23. An ultrasonic probe as claimed in claim 21, wherein said acoustic medium comprises a physiological salt solution.

24. An ultrasonic probe as claimed in claim 1, wherein said refracting member is made of a material having an acoustic impedance substantially equal to that of a human body.

25. An ultrasonic probe as claimed, in claim 1, wherein said driving means rotates said refracting member at a constant speed.

26. An ultrasonic probe as claimed in claim 1, wherein said piezoelectric element emits the ultrasonic beam at a predetermined time interval.

27. An ultrasonic probe comprising:
a housing;
a piezoelectric element provided in said housing, said piezoelectric element having an emitting surface adapted for emitting an ultrasonic beam;
a first refracting member rotatably provided in said housing, said first refracting member having (a) a first flat surface opposed to said piezoelectric element emitting surface adapted so the said ultrasonic beam passes through said first flat surface and (b) a second undulating surface from which said ultrasonic beam is focused at different focal points when one revolution of said refracting member is completed; and
a second refracting member rotatably provided in said housing and opposed to said first refracting member so that said second refracting member has an axis identical to that of said first refracting member, said second refracting member having a third flat surface which receives and passes the ultrasonic beam emitted from said second undulating surface of said first refracting member, and a fourth undulating surface from which said ultrasonic beam from said third flat surface is deflected wherein a deflection angle between (a) an axis perpendicular to said emitting surface of said piezoelectric element and (b) said deflected ultrasonic beam emitted from said fourth undulating surface changes as said second refracting member rotates.

28. An ultrasonic probe as claimed in claim 27, further comprising:
first driving means for rotating said first refracting member; and
second driving means for rotating said second refracting member.

29. An ultrasonic probe as claimed in claim 28, wherein said first driving means rotates said first refracting member at a rotational speed equal to a rotational speed of said second refracting member rotated by said second driving means.

30. An ultrasonic probe as claimed in claim 28, wherein said first driving means rotates said first refracting member in a direction equal to a direction in which said second driving means rotates said second refracting member.

31. An ultrasonic probe as claimed in claim 27, wherein said piezoelectric element has a size sufficient to partially project the ultrasonic beam onto said first surface of said first refracting member.

32. An ultrasonic probe as claimed in claim 27, further comprising an acoustic medium provided in said housing so that said first refracting member, said second refracting member and said piezoelectric member are surrounded by said acoustic medium.

33. An ultrasonic probe as claimed in claim 32, wherein each of said first refracting member and said second refracting member has a refractive index different from the refractive index of said acoustic medium.

34. An ultrasonic probe as claimed in claim 27, wherein each of said first refracting member and said second refracting member has an acoustic impedance substantially equal to an acoustic impedance of the human body.

* * * * *